US009814376B2

(12) United States Patent
Kubo

(10) Patent No.: US 9,814,376 B2
(45) Date of Patent: *Nov. 14, 2017

(54) ENDOSCOPE SYSTEM AND METHOD FOR OPERATING THE SAME

(71) Applicant: FUJIFILM Corporation, Tokyo (JP)

(72) Inventor: Masahiro Kubo, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/927,914

(22) Filed: Oct. 30, 2015

(65) Prior Publication Data

US 2016/0120398 A1    May 5, 2016

(30) Foreign Application Priority Data

Oct. 31, 2014  (JP) ................................. 2014-222466

(51) Int. Cl.
*A61B 1/045* (2006.01)
*H04N 9/00* (2006.01)
*A61B 1/06* (2006.01)
*H04N 5/225* (2006.01)
*A61B 1/00* (2006.01)
*H04N 5/345* (2011.01)

(52) U.S. Cl.
CPC ........ *A61B 1/0638* (2013.01); *A61B 1/00006* (2013.01); *A61B 1/045* (2013.01); *H04N 5/2256* (2013.01); *H04N 5/3456* (2013.01); *H04N 2005/2255* (2013.01)

(58) Field of Classification Search
CPC ... A61B 1/00006; A61B 1/045; A61B 1/0638; H04N 2005/2255; H04N 5/2256; H04N 9/00
USPC ............................................................ 348/68
See application file for complete search history.

(56) References Cited

U.S. PATENT DOCUMENTS

| | | | | |
|---|---|---|---|---|
| 5,519,514 A | * | 5/1996 | TeWinkle | H04N 1/486 348/E3.019 |
| 6,970,195 B1 | * | 11/2005 | Bidermann | H04N 1/00307 348/302 |
| 2006/0000989 A1 | * | 1/2006 | Kuriyama | G01N 21/8806 250/559.34 |

(Continued)

FOREIGN PATENT DOCUMENTS

JP        2012-125395 A       7/2012

*Primary Examiner* — Mohammed Rahaman
*Assistant Examiner* — James Boylan
(74) *Attorney, Agent, or Firm* — Birch, Stewart, Kolasch & Birch, LLP

(57) ABSTRACT

A light source unit is provided with a first light source, a second light source, and a third light source that emit red light, green light, and blue light, respectively, as illumination light. A light source controller controls emission intensity and emission timing of the illumination light to make an emission period of the red light longer than an emission period of each of the green light and the blue light. An image sensor is capable of separately receiving the light of each color reflected from an object of interest irradiated with the illumination light and capable of separately changing a light-receiving period of the light of each color. An imaging controller makes the light-receiving period of at least the red light coincide with the emission period of the red light.

8 Claims, 14 Drawing Sheets

(56) References Cited

U.S. PATENT DOCUMENTS

| | | | |
|---|---|---|---|
| 2006/0192867 A1* | 8/2006 | Yosefin | H04N 5/3535 348/273 |
| 2010/0097454 A1* | 4/2010 | Kubo | A61B 1/00188 348/65 |
| 2010/0130819 A1* | 5/2010 | Kubo | A61B 1/00009 600/109 |
| 2010/0141747 A1* | 6/2010 | Kubo | A61B 1/00009 348/68 |
| 2010/0256449 A1* | 10/2010 | Kubo | A61B 1/042 600/160 |
| 2010/0312058 A1* | 12/2010 | Kubo | A61B 1/0638 600/178 |
| 2011/0134298 A1* | 6/2011 | Aoyama | H01L 27/14609 348/311 |
| 2011/0263943 A1* | 10/2011 | Yamaguchi | A61B 1/04 600/178 |
| 2012/0157774 A1 | 6/2012 | Kaku | |
| 2013/0300849 A1* | 11/2013 | Ono | A61B 1/00006 348/68 |
| 2014/0063216 A1* | 3/2014 | Kubo | A61B 1/00009 348/71 |
| 2014/0163319 A1* | 6/2014 | Blanquart | A61B 1/0638 600/109 |
| 2014/0253580 A1* | 9/2014 | Kubo | G06T 11/001 345/590 |
| 2014/0316196 A1* | 10/2014 | Wichern | A61B 1/05 600/109 |
| 2016/0143520 A1* | 5/2016 | Masaki | A61B 1/0638 600/109 |

\* cited by examiner

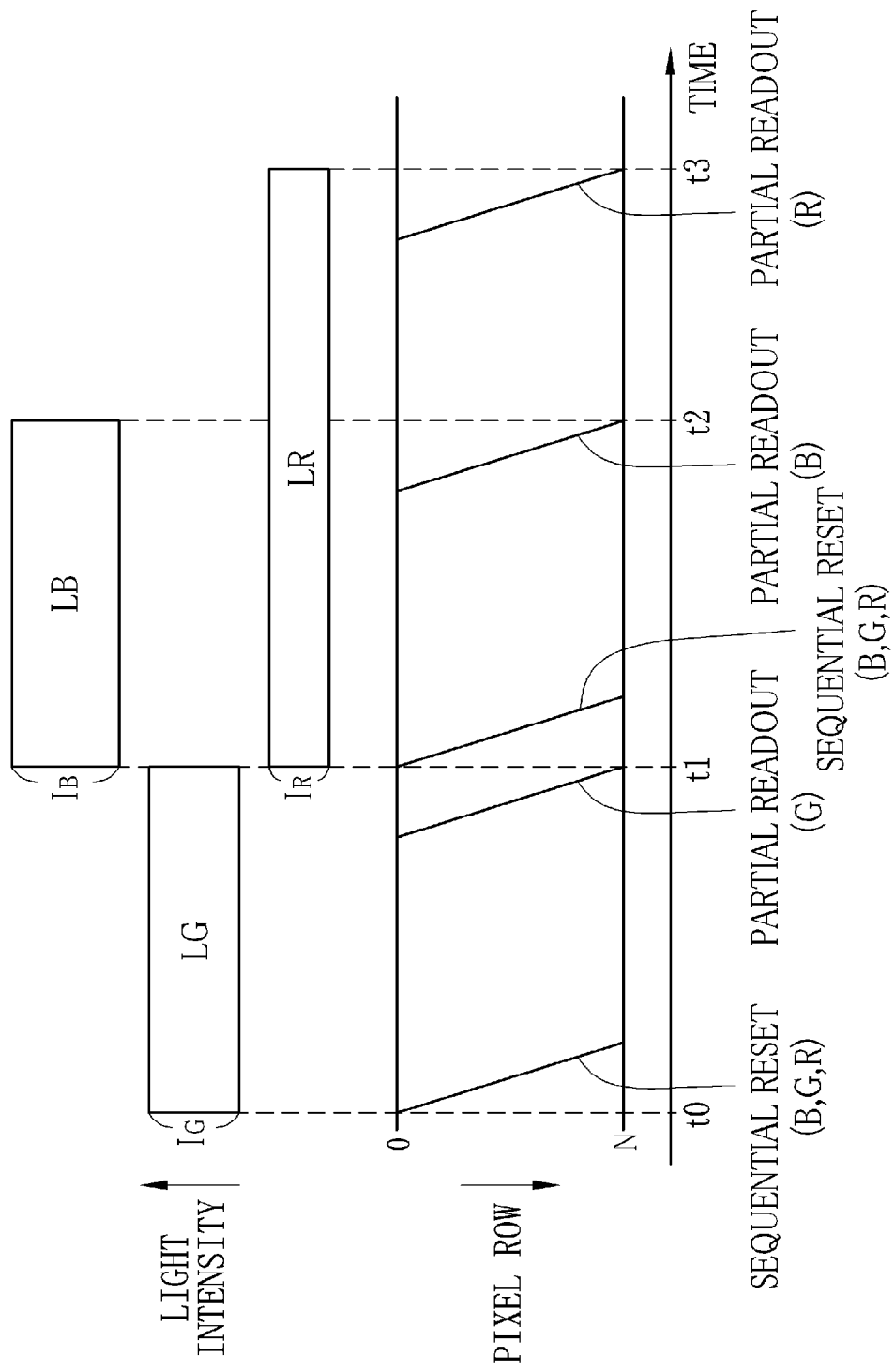

ENDOSCOPE SYSTEM AND METHOD FOR OPERATING THE SAME

CROSS-REFERENCE TO RELATED APPLICATIONS

The present application claims priority under 35 U.S.C. §119 to Japanese Patent Application No. 2014-222466, filed Oct. 31, 2014. Each of the above application(s) is hereby expressly incorporated by reference, in its entirety, into the present application.

BACKGROUND OF THE INVENTION

1. Field of the Invention

The present invention relates to an endoscope system and a method for operating an endoscope system.

2. Description Related to the Prior Art

In medical fields, diagnoses using an endoscope system that comprises a light source device for an endoscope (hereinafter simply referred to as the light source device), an endoscope, and a processor device, are widely performed. The light source device generates illumination light to be applied to an object of interest (hereinafter referred to as the object) such as mucosa in a body cavity. The endoscope comprises an image sensor for imaging the object irradiated with the illumination light.

An endoscope system comprising a light source device that emits white light (the illumination light) and a simultaneous-type color sensor (the image sensor) has been known. The color sensor separates the light incident on the endoscope from the object into blue (B) light, green (G) light, and red (R) light and captures them simultaneously.

The light quantities of the B, G, and R light differ from each other in the white light from the light source device depending on the properties of the light sources, and the spectral sensitivity (spectral response) of the image sensor varies according to the color of light. For these reasons, a light source device capable of separately adjusting a light quantity of light of each color has been known (see US2012/0157774 (corresponding to Japanese Patent Unexamined Application Publication No. 2012-125395)). The light source device described is capable of adjusting the light quantity of each of the B, G, and R light included in the white light. The US2012/0157774 describes that the light quantity of the B light is preferably greater than that of the G light and the light quantity of the G light is preferably greater than that of the R light (that is, the B light>the G light>the R light).

Reflectance of the object, for example, mucosal tissue and the like of large intestine decreases as the wavelengths of the illumination light become shorter. However, the light reflected from the surface layer of the mucosal tissue is mostly the light of short wavelengths. Because the surface layer of the mucosal tissue includes the microstructure such as capillaries (capillary vessels), it is preferred that the light quantities among the light of the respective colors satisfy the relationship the B light>the G light>the R light in generating an image including the microstructure as described in the US2012/0157774. In this case, the relationship among the signal levels of the image signals from the image sensor is expressed as "the B pixel signals>the G pixel signals>the R pixel signals". The signal level of the R pixel signals may be low.

The US2012/0157774 describes that a special image is generated from the B pixel signals and the G pixel signals. The special image eliminates the R pixel signals, so that there is little degradation in image quality due to the above-described relationship among the light quantities. Recently, however, attention has been focused on a color enhancement process for performing image processing on an image captured using the white light, to clarify a border between a normal site and a lesion. In a case where the color enhancement process is performed, it is preferred that the image quality of a red image is at substantially the same level as those of the blue and green images.

SUMMARY OF THE INVENTION

An object of the present invention is to provide an endoscope system that improves image quality of a red image and generates an image of high image quality through a color enhancement process and a method for operating an endoscope system.

In order to achieve the above and other objects, an aspect of the present invention provides an endoscope system comprising a light source unit, a light source controller, an image sensor, and an imaging controller. The light source unit emits each of first light, second light, and third light as illumination light. The first, second, and third light are different in color from each other. The light source controller is configured to control emission intensity and emission timing of the illumination light to make an emission period of the first light longer than an emission period of each of the second light and the third light. The image sensor is configured to be capable of separately receiving light of each color reflected from an object of interest irradiated with the illumination light and capable of separately changing a light-receiving period of the light of each color. The imaging controller is configured to make the light-receiving period of at least the first light on the image sensor coincide with the emission period of the first light.

It is preferred that the light source controller makes emission start timing of the second light coincide with emission start timing of the third light.

It is preferred that the light source controller makes emission end timing of the second light different from emission end timing of the third light.

It is preferred that the light source controller ends the emission of the third light after ending the emission of the second light.

It is preferred that the light source controller makes the emission intensity of the first light less than the emission intensity of each of the second light and the third light.

It is preferred that the imaging controller makes the light-receiving period of the first light on the image sensor coincide with the emission period of the first light, and makes the light-receiving period of the second light on the image sensor coincide with the emission period of the second light, and makes the light-receiving period of the third light on the image sensor coincide with the emission period of the third light.

It is preferred that the first light is red light, the second light is green light, and the third light is blue light.

An aspect of the present invention provides a method for operating an endoscope system comprising a step of controlling emission intensity and emission timing of the illumination light to make an emission period of the first light longer than an emission period of each of the second light and the third light and a step of making the light-receiving period of at least the first light on the image sensor coincide with the emission period of the first light. The endoscope system comprises a light source unit and an image sensor. The light source unit emits each of first light, second light, and third light as illumination light. The first, second, and third light are different in color from each other. The image sensor is configured to be capable of separately receiving light of each color reflected from an object of interest irradiated with the illumination light and capable of separately changing a light-receiving period of the light of each color.

According to the aspects of the present invention, the emission period of the first light (red light) is made longer than the emission period of each of the second light and the third light. At least the light-receiving period of the first light on the image sensor, which is capable of separately receiving the light of each color and separately changing the light-receiving period of the light of each color, coincides with the emission period of the first light. Thereby the image quality of the red image is improved, and the image of high image quality is generated by the color enhancement process.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein:

FIG. 14 illustrates the emission timing and the imaging timing in an example in which green light is emitted independently.

DESCRIPTION OF THE PREFERRED EMBODIMENTS

First Embodiment

Figure 1:
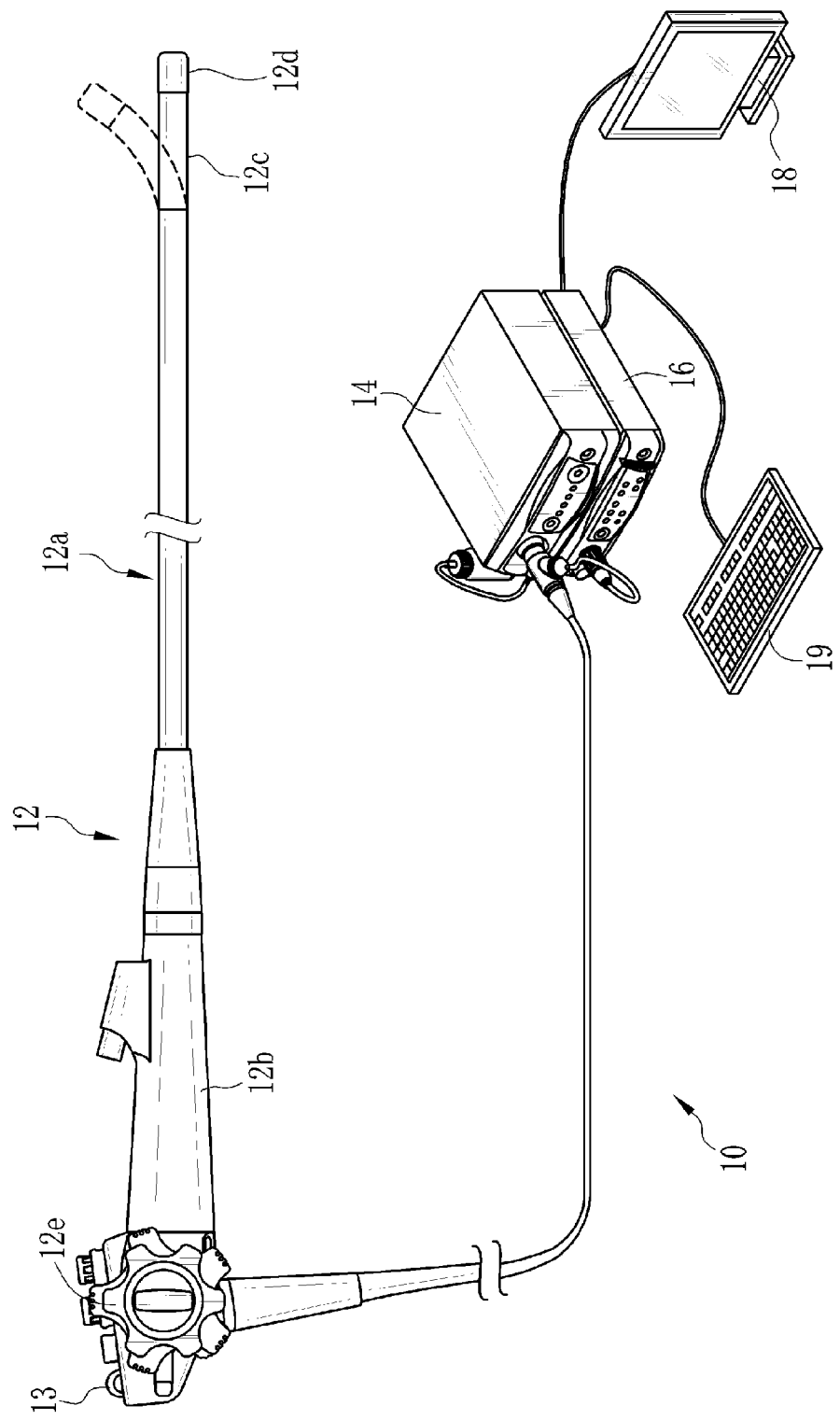
FIG. 1 is an external view of an endoscope system.

In FIG. 1, an endoscope system 10 comprises an endoscope 12, a light source device 14 for an endoscope, a processor device 16, a monitor 18, and a console 19. The endoscope 12 is connected optically to the light source device 14 and electrically to the processor device 16. The endoscope 12 comprises an insertion section 12a to be inserted into a body cavity, a control handle unit 12b provided at the proximal end of the insertion section 12a, a flexible portion 12c, which is provided on the distal side of the insertion section 12a, and a distal end portion 12d coupled to the flexible portion 12c.

The flexible portion 12c is bent by operating an angle knob 12e of the control handle unit 12b. Thereby the distal end portion 12d is directed to a desired direction. The control handle unit 12b is provided with the angle knob 12e and a zoom operating section 13.

The light source device 14 generates white light as illumination light and supplies the illumination light to the endoscope 12. The illumination light supplied to the endoscope 12 is transmitted to the distal end portion 12d and applied to an object of interest (hereinafter referred to as the object) from the distal end portion 12d.

The processor device 16 is electrically connected to the monitor 18 and the console 19. The monitor 18 outputs image(s) of the object, information associated with the corresponding image(s), and the like. The console 19 functions as a UI (user interface), which receives input operation such as setting a function. Note that an external storage unit (not shown) for recording the images and the image information may be connected to the processor device 16.

Figure 2:
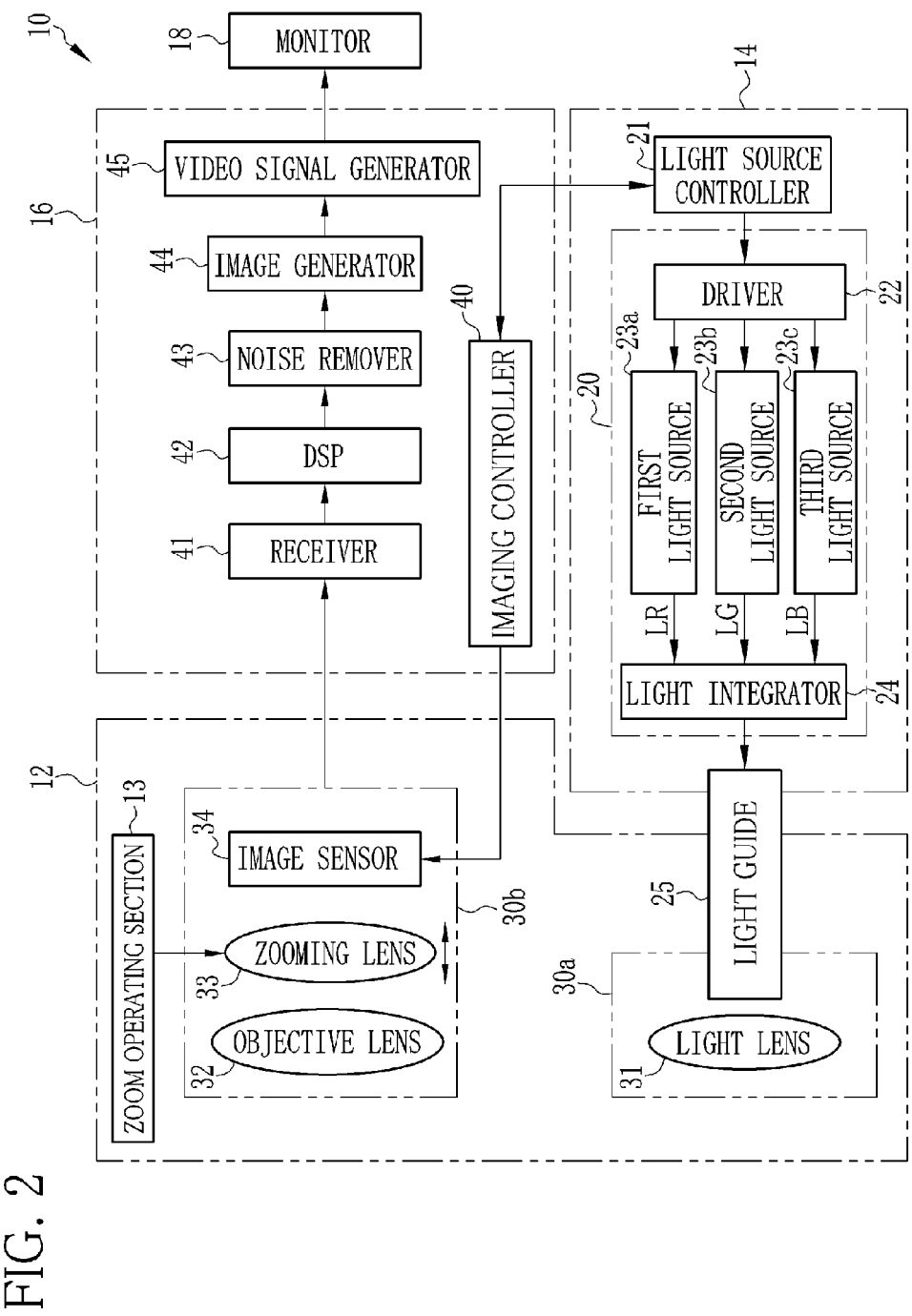
FIG. 2 is a block diagram illustrating functions of the endoscope system.

As illustrated in FIG. 2, the light source device 14 comprises a light source unit 20, which generates the illumination light for illuminating the object, and a light source controller 21, which controls light emission intensity (hereinafter simply referred to as the emission intensity) and light emission timing (hereinafter simply referred to as the emission timing). The light source unit 20 comprises a driver 22, first to third light sources 23a to 23c, and a light integrator 24. Based on the control of the light source controller 21, the driver 22 drives each of the first to third light sources 23a to 23c.

The first light source 23a is a red LED (Light-emitting diode), which emits red light (first light) LR. For example, the red light LR is in a wavelength range of 615 nm to 635 nm and has the center wavelength of 620±10 nm. The second light source 23b is a green LED, which emits green light (second light) LG. For example, the green light LG is in a wavelength range of 500 nm to 600 nm and has the center wavelength of 520±10 nm. The third light source 23c is a blue LED, which emits blue light (third light) LB. For example, the blue light LB is in a wavelength range of 440 nm to 470 nm and has the center wavelength of 455±10 nm.

The light integrator 24 is composed of a dichroic mirror and the like and combines the light paths of the light from the first to third light sources 23a to 23c. The light from the light integrator 24 is supplied as the illumination light to a light guide 25 extending inside the insertion section 12a.

The light guide 25 is incorporated in the endoscope 12 and transmits the illumination light to the distal end portion 12d of the endoscope 12. Note that a multimode fiber may be used as the light guide 25. For example, a small-diameter fiber cable with the core diameter 105 µm, the clad diameter 125 µm, and the outer diameter φ 0.3 to 0.5 mm (including a protection layer, being a jacket) may be used.

The distal end portion 12d of the endoscope 12 comprises an illumination optical system 30a and an imaging optical system 30b. The illumination optical system 30a has a light lens 31. The illumination light transmitted through the light guide 25 is applied to the object through the light lens 31. The imaging optical system 30b has an objective lens 32, a zooming lens 33, and an image sensor 34. The light reflected from the object is incident on the image sensor 34 through the objective lens 32 and the zooming lens 33. Thereby a light image of the object is formed on an imaging surface (not shown) of the image sensor 34. Note that the zooming lens 33 is movable between the telephoto end and the wide angle end in accordance with the operation of the zoom operating section 13, to magnify or reduce the size of the light image of the object formed on the imaging surface of the image sensor 34.

The image sensor 34 is a simultaneous-type color sensor, which receives the light reflected from the object irradiated with the illumination light and outputs image signals. The image sensor 34 is capable of separately receiving the light of each color, blue (B), green (G), and red (R), and capable of separately changing a light-receiving period (or exposure time) for receiving the light of each color. A CMOS (Complementary Metal-Oxide Semiconductor) image sensor may be used as the image sensor 34. The image sensor 34 outputs RGB image signals as the image signals. The RGB image signals are composed of B pixel signals, G pixel signals, and R pixel signals.

The processor device 16 comprises an imaging controller 40, a receiver 41, a DSP (Digital Signal Processor) 42, a noise remover 43, an image generator 44, and a video signal generator 45.

The imaging controller 40 controls imaging timing of the image sensor 34. The receiver 41 receives digital RGB image signals outputted from the image sensor 34 of the endoscope 12. The DSP 42 performs various types of image processing such as defect correction process, offset processing, gain correction process, linear matrix processing, gamma conversion process, and demosaicing process on the received RGB image signals.

In the defect correction process, signals of defective pixels of the image sensor 34 are corrected. In the offset processing, dark current components are removed from the RGB image signals that have been subjected to the defect correction process. Thereby an accurate zero level is set. In the gain correction process performed after the offset processing, signal level(s) is adjusted or corrected by multiplying the RGB image signals by a specific gain. After the gain correction process, the RGB image signals are subjected to the linear matrix processing to increase color reproducibility. Thereafter, brightness and saturation are adjusted or corrected through the gamma conversion process. After the linear matrix processing, the demosaicing process (also referred to as equalization process or synchronization process) is performed on the RGB image signals. Thereby signals of RGB colors are generated for each pixel.

The noise remover 43 performs a noise removal process (for example, a moving average method or a median filter method) on the RGB image signals that have been subjected to the demosaicing process and the like performed by the DSP 42, to remove noise. The RGB image signals from which the noise has been removed are inputted to the image generator 44.

The image generator 44 performs a color conversion process, a color enhancement process, and a structure enhancement process on the RGB image signals inputted from the noise remover 43, to generate an image. The color conversion process is performed on the RGB image signals through 3×3 matrix processing, a tone conversion process, a three-dimensional LUT (lookup table) process, or the like. The color enhancement process is performed on the RGB image signals that have been subjected to the color conversion process. The structure enhancement process is to enhance the structure (e.g. surface blood vessels, pit patterns, or the like) of the object. The structure enhancement process is performed on the RGB image signals that have been subjected to the color enhancement process.

The image generated by the image generator 44 is inputted to the video signal generator 45. The video signal generator 45 converts each image into a video signal to be displayed on the monitor 18. The monitor 18 displays the image based on the video signal inputted from the video signal generator 45.

Figure 3:
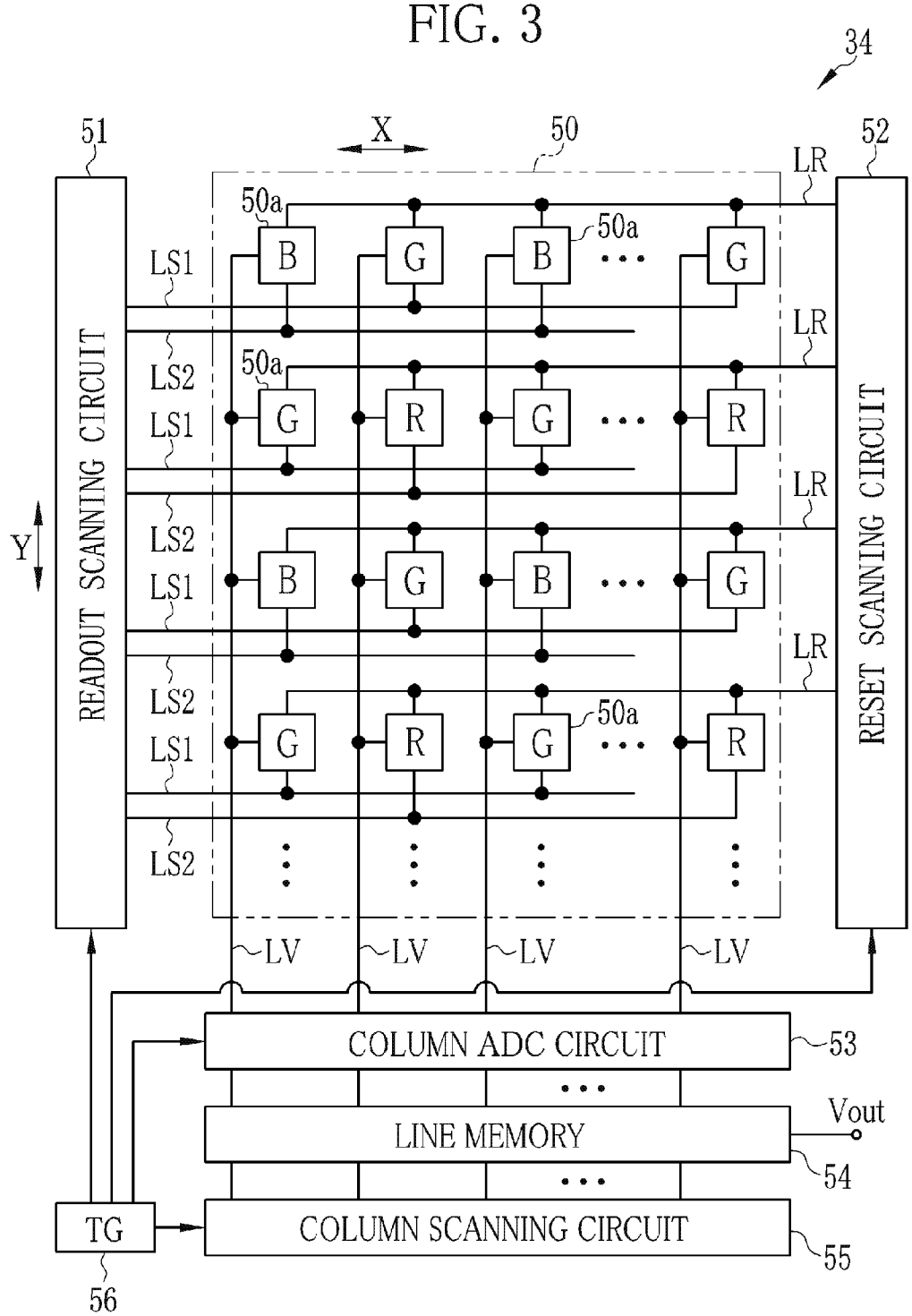
FIG. 3 illustrates configuration of an image sensor.

In FIG. 3, the image sensor 34 comprises a pixel array 50, a readout scanning circuit 51, a reset scanning circuit 52, a column ADC (Analog-to-digital converter) circuit 53, a line memory 54, a column scanning circuit 55, and a timing generator (TG) 56. In response to or based on an imaging control signal inputted from the imaging controller 40 of the processor device 16, the TG 56 generates timing signals for controlling respective sections.

The pixel array 50 is composed of a plurality of pixels 50a arranged in a matrix in two dimensions, in a row direction (X direction) and a column direction (Y direction). The pixel array 50 is provided on the imaging surface of the image sensor 34. In the pixel array 50, first row selection lines LS1, second row selection lines LS2, and row reset lines LR are disposed in the row direction. Column signal lines LV are disposed in the column direction.

Each pixel row is provided with the first row selection line LS1, the second row selection line LS2, and the row reset line LR. Each pixel column is provided with the column signal line LV. Here, the pixel row refers to a row of the pixels 50a that are arranged in the row direction. The pixel column refers to a column of the pixels 50a that are arranged in the column direction.

Figure 4:
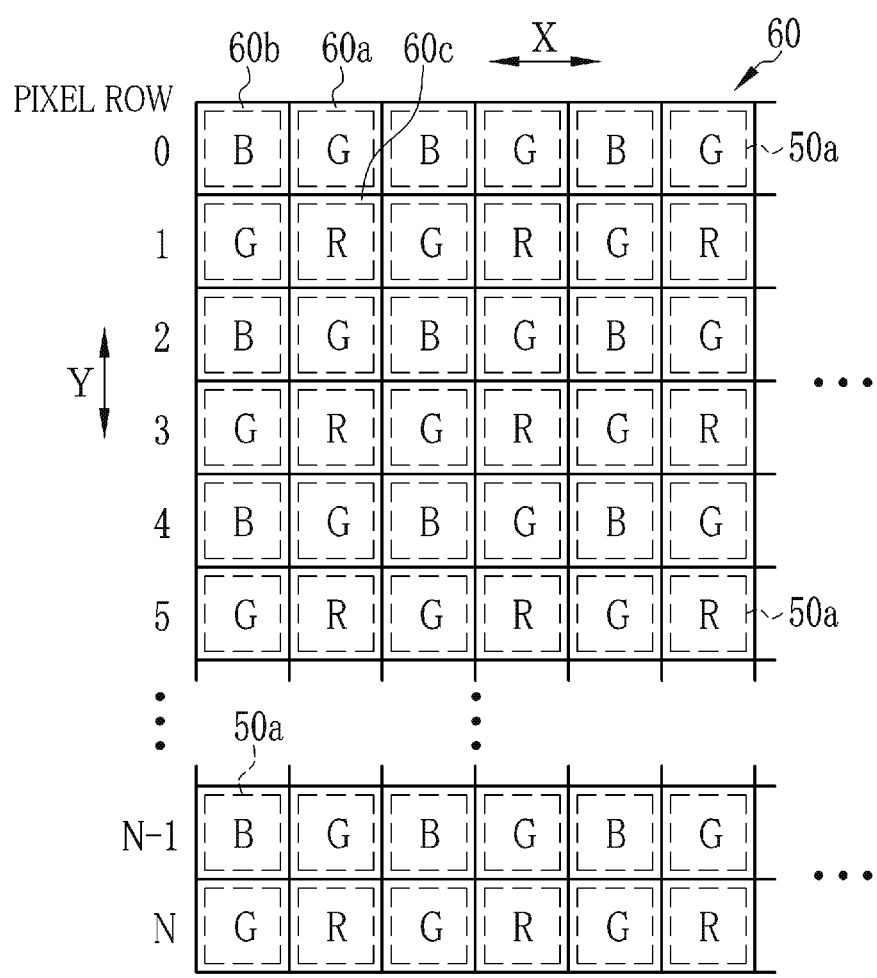
FIG. 4 illustrates a color arrangement of color filters.

As illustrated in FIG. 4, a color filter array 60 is provided on the light incident side of the pixel array 50. The color filter array 60 comprises green (G) filters 60a, blue (B) filters 60b, and red (R) filters 60c. One of the filters 60a, 60b, and 60c is disposed over each pixel 50a. The filters 60a, 60b, and 60c of the color filter array 60 are arranged in a Bayer pattern, in which the G filters 60a are arranged in an alternate checkered pattern over the corresponding pixels and the B and R filters 60b and 60c are arranged over the remaining pixels 50a such that the B filters 60b and R filters 60c form respective square lattice patterns.

Figure 5:
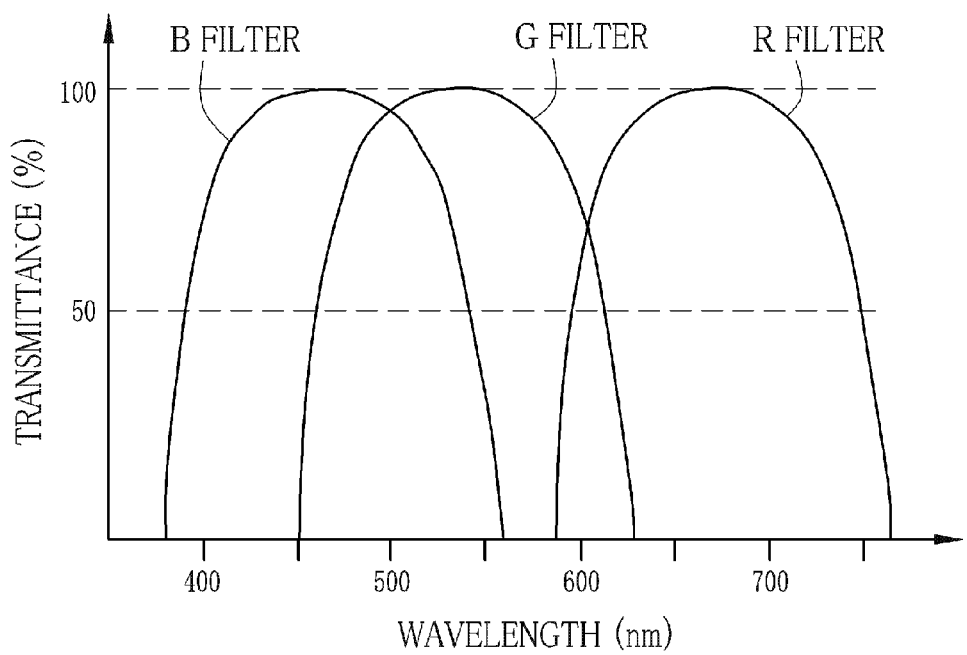
FIG. 5 illustrates spectral characteristics of the color filters.

The color filter array 60 has spectral characteristics illustrated in FIG. 5. The G filter 60a has high transmittance to light in a wavelength range of approximately 450 to 630 nm. The B filter 60b has high transmittance to light in a wavelength range of approximately 380 to 560 nm. The R filter 60c has high transmittance to light in a wavelength range of approximately 580 to 760 nm.

Hereinafter, the pixel 50a over which the G filter 60a is disposed is referred to as the G pixel. The pixel 50a over which the B filter 60b is disposed is referred to as the B pixel. The pixel 50a over which the R filter 60c is disposed is referred to as the R pixel. In each of the even-numbered (0, 2, 4, . . . , N−1) pixel rows, the B and G pixels are arranged alternately. In each of the odd-numbered (1, 3, 5, . . . , N) pixel rows, the G and R pixels are arranged alternately.

The pixels 50a of one pixel row are connected to a single corresponding row reset line LR. Of the pixels 50a of one pixel row, the G pixels are connected to a single corresponding first row selection line LS1. The B pixels of one pixel row are connected to a single corresponding second row selection line LS2. The R pixels of one pixel row are connected to a single corresponding second row selection line LS2.

Figure 6:
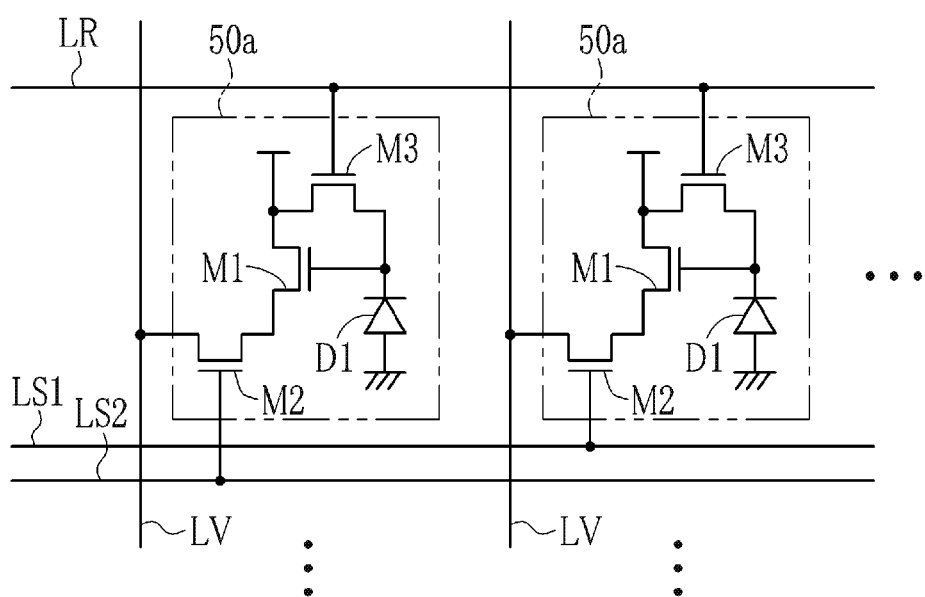
FIG. 6 illustrates configuration of pixels of the image sensor.

As illustrated in FIG. 6, each pixel 50a has a photodiode D1, an amplifying transistor M1, a pixel selection transistor M2, and a reset transistor M3. The photodiode D1 photoelectrically converts the incident light into a signal charge in accordance with the quantity of the incident light and stores the signal charge. The amplifying transistor M1 converts the signal charge stored in the photodiode D1 into a voltage value (pixel signal). The pixel selection transistor M2 is controlled through the first row selection line LS1 or the second row selection line LS2 and allows the pixel signal, which is generated by the amplifying transistor M1, to be outputted to the column signal line LV. The reset transistor M3 is controlled through the row reset line LR and discharges (resets) the signal charge, which is stored in the photodiode D1, to a power line.

The readout scanning circuit 51 generates a row selection signal in response to the timing signal inputted from the TG 56. At the time of a signal readout operation for reading out the pixel signals, the readout scanning circuit 51 supplies the row selection signal to the first row selection line LS1 or the second row selection line LS2. Thereby the readout scanning circuit 51 allows the pixel signals of the pixels 50a connected to the first row selection line LS1 or the second row selection line LS2 to which the row selection signal has been supplied, to be outputted to the column signal line LV.

In response to the timing signal inputted from the TG 56, the reset scanning circuit 52 generates a reset signal. At the time of a reset operation for resetting the pixels, the reset scanning circuit 52 supplies the reset signal to the row reset line LR. Thereby the pixels 50a connected to the row reset line LR to which the reset signal has been supplied are reset.

The pixel signals that are outputted to the column signal line LV at the time of the signal readout operation are inputted to the column ADC circuit 53. Each column signal line LV is connected to the column ADC circuit 53. The column ADC circuit 53 compares the pixel signals inputted from each column signal line LV with a reference signal (a ramp wave), the slope of which changes in a stepwise manner with time, to convert the pixel signals into digital signals and outputs the digital signals to the line memory 54.

The line memory 54 stores the pixel signals of one row that have been digitized by the column ADC circuit 53. In response to the timing signal inputted from the TG 56, the column scanning circuit 55 scans the line memory 54, thereby allowing the pixel signals to be outputted sequentially from an output terminal Vout. The pixel signals of one frame outputted from the output terminal Vout correspond to the RGB image signals described above.

The image sensor 34 is capable of performing "sequential readout" and "partial readout" in reading out the signals. In the "sequential readout", the readout scanning circuit 51 sequentially chooses a pair of the first and second row selection lines LS1 and LS2 of each pixel row and the row selection signal S1 is supplied simultaneously to each of the first and second row selection lines LS1 and LS2 chosen. Thereby the pixel signals are read out sequentially on a pixel row by pixel row basis from the first pixel row "0" to the last pixel row "N". Thus the pixel signals are read out from all of the pixels 50a of the pixel array 50.

The partial readout enables selectively reading out the pixels of a specific color in the pixel array 50. For example, in order to read out only the R pixels of the pixel array 50, the readout scanning circuit 51 sequentially chooses only the second row selection lines LS2 of the odd-numbered (1, 3, 5, . . . , N) pixel rows and supplies the row selection signal S1 to each of the second row selection lines LS2 chosen. Thereby the pixel signals of only the R pixels of all the pixels 50a are read out sequentially on a pixel row by pixel row basis.

In this case, only the pixel signals (R pixel signals) read out from the R pixels are stored in the line memory 54. The column scanning circuit 55 scans the line memory 54 every time the pixel signals (R pixel signals) of one of the odd-numbered pixel rows are stored in the line memory 54.

The partial readout enables selectively reading out the pixels of two colors in the pixel array 50. For example, in order to read out the B pixels and the G pixels of the pixel array 50, the readout scanning circuit 51 chooses the first and second row selection lines LS1 and LS2 for each even-numbered (0, 2, 4, . . . , N−1) pixel row sequentially and chooses the first row selection line LS1 for each odd-numbered (1, 3, 5, . . . , N) pixel row sequentially, and supplies the row selection signal S1 to each row selection line chosen. Thereby the pixel signals of only the B pixels and the G pixels of all the pixels 50a are read out sequentially on a pixel row by pixel row basis.

In this case, at the time of the readout from the even-numbered pixel row, the pixel signals (the B pixel signals and the G pixel signals) readout from the B pixels and the G pixels are stored in the line memory 54. At the time of the readout from the odd-numbered pixel row, only the pixel signals (the G pixel signals) read out from the G pixels are stored in the line memory 54. The column scanning circuit 55 scans the line memory 54 every time the pixel signals of one pixel row (the even-numbered or odd-numbered pixel row) are stored in the line memory 54. Note that, in order to read out the B pixels and the G pixels, only the even-numbered pixel rows may be read out, without the readout of the odd-numbered pixel rows.

The image sensor 34 is capable of performing "sequential reset" and "entire (collective and simultaneous) reset". In the sequential reset, the reset scanning circuit 52 sequentially chooses the row reset lines LR and supplies the reset signal S2 to each row reset line LR chosen. Thereby, in the sequential reset, the pixel rows are sequentially reset on a pixel row by pixel row basis from the first pixel row "0" to the last pixel row "N".

In the entire reset, the reset scanning circuit 52 chooses all of the row reset lines LR and simultaneously supplies the reset signal S2 to every row reset line LR. Thereby the pixels of all the pixel rows of the pixel array 50 are reset collectively and simultaneously.

Although not illustrated in FIG. 3, note that the image sensor 34 is provided with a correlated double sampling (CDS) circuit and an automatic gain control (AGC) circuit as necessary. The CDS circuit performs correlated double sampling on the pixel signals outputted from the pixels 50a to the corresponding column signal line LV. The AGC circuit adjusts the gain of the pixel signal that has been subjected to the correlated double sampling.

The light source controller 21 and the imaging controller 40 are electrically connected to each other. The imaging controller 40 controls the imaging timing of the image sensor 34 in accordance with the emission timing of the illumination light of the light source device 14, which is controlled by the light source controller 21.

Figure 7:
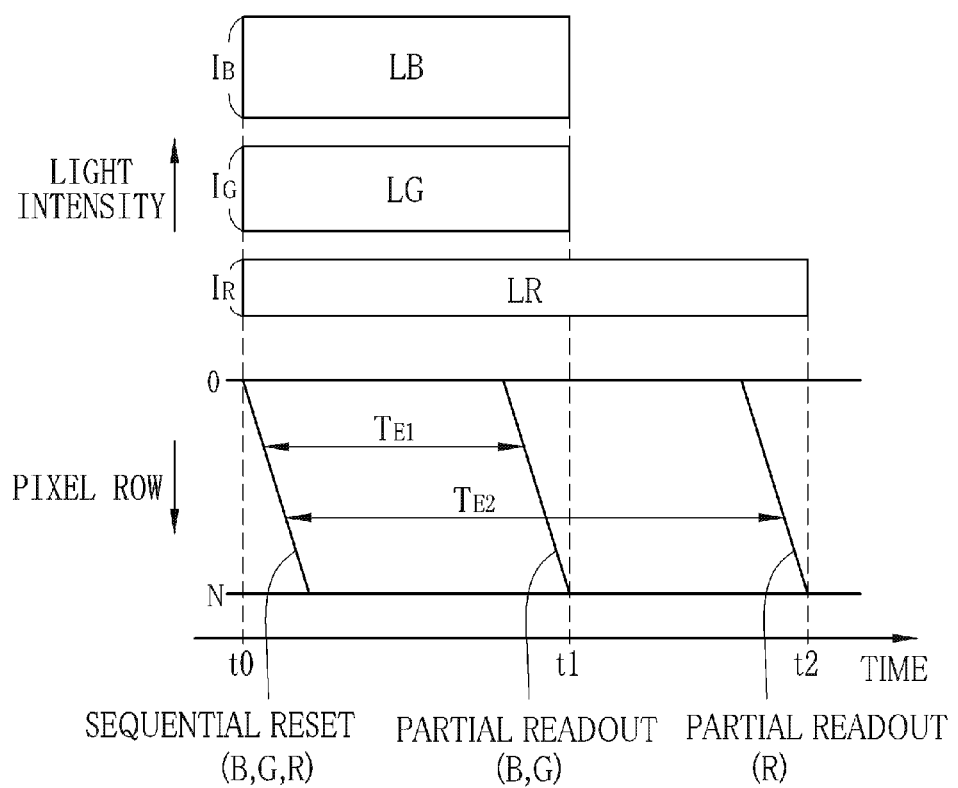
FIG. 7 illustrates emission timing and imaging timing.

Hereinafter, the emission timing controlled by the light source controller 21 and the imaging timing controlled by the imaging controller 40 are described. As illustrated in FIG. 7, the light source controller 21 controls the driver 22 to allow the first to third light sources 23a to 23c to simultaneously start the emissions of the red light LR, the green light LG, and the blue light LB, respectively, from the time t0 (in other words, emission start timing is the same).

At this time, the light source controller 21 makes an emission intensity $I_B$ of the blue light LB greater than an emission intensity $I_G$ of the green light LG and makes the emission intensity $I_G$ of the green light LG greater than an emission intensity $I_R$ of the red light LR (that is, $I_3 > I_G > I_R$).

Figure 8:
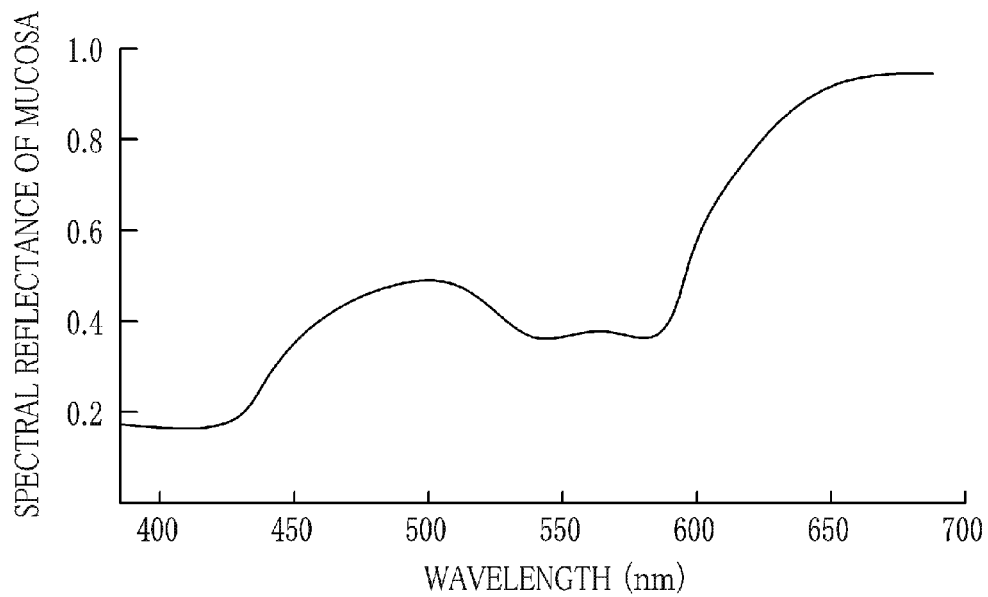
FIG. 8 is a graph illustrating spectral reflectance of mucosa.

Although the reflectance of the mucosal tissue and the like of the large intestine, being the object of interest, decreases as the wavelengths become shorter as illustrated in FIG. 8, most of the light reflected from the surface layer of the mucosal tissue has short wavelengths. The surface layer of the mucosal tissue includes a microstructure such as capillaries and the like. To generate the image including the microstructure, the relationship $I_B>I_G>I_R$ is satisfied.

The red light LR, the green light LG, and the blue light LB emitted from the first to third light sources 23a to 23c are combined by the light integrator 24 into the white light. The white light, being the white illumination light, is supplied to the light guide 25. The white illumination light is emitted from the distal end portion 12d of the endoscope 12 to illuminate the object.

The imaging controller 40 controls and allows the image sensor 34 to start the reset operation (sequential reset) from the time t0. Thereby all of the pixel rows are reset sequentially on a pixel row by pixel row basis. The unnecessary charges are discharged from the pixels 50a of each pixel row. Thereby the pixels 50a of each pixel row start storing the charges (exposure state). After a lapse of the first exposure time $T_{E1}$ from the time t0, the imaging controller 40 controls and allows the image sensor 34 to start the signal readout operation of the B pixels and the G pixels only (partial readout). Thereby the image sensor 34 outputs the digital B pixel signals and the digital G pixel signals. At this time, the readout of the R pixels is not performed, so that the exposure of the R pixels is continued.

The light source controller 21 controls the driver 22 to stop the emission operations of the second light source 23b and the third light source 23c at the time t1, at which the readout of the last pixel row N is finished. Thereby the light source controller 21 ends the emissions of the green light LG and the blue light LB.

Then, after a lapse of the second exposure time $T_{E2}$ from the time t0, the imaging controller 40 controls and allows the image sensor 34 to start the signal readout operation (partial readout) of the R pixels only. Thereby, the image sensor 34 outputs the digital R pixel signals. The light source controller 21 controls the driver 22 to stop the emission operation of the first light source 23a at the time t2, at which the readout of the last pixel row N is finished. Thereby the light source controller 21 ends the emission of the red light LR.

The light-receiving period (exposure time) of each of the green light LG and the blue light LB on the image sensor 34 is from the time t0 to the time t1 as described above and coincides with the emission period of each of the green light LG and the blue light LB from the light source device 14. The light-receiving period of the red light LR on the image sensor 34 is from the time t0 to the time t2 and coincides with the emission period of the red light LR from the light source device 14.

Each of the emission period of the blue light LB and the emission period of the green light LG is shorter than the emission period of the red light LR because the blue light (LB) component and the green light (LG) component of the light reflected from the object include a high amount of image information (high frequency components) about the structure of the surface and subsurface (intermediate) layers of the mucosa and such image information (or image) is likely to be affected by blur (motion blur or camera shake due to an operator, or the like).

On the other hand, the red light (LR) component of the light reflected from the object include a high amount of image information (low frequency components) about a deep layer of the mucosa and there is little influence of the blur. The emission period of the red light LR is made longer than each of the emission period of the blue light LB and the emission period of the green light LG, so that the exposure amount (dose) of the red light LR on the image sensor 34 is increased. Thereby the sensitivity (the S/N ratio) is improved. Note that the exposure amount is proportionate to the product of the light intensity and the emission period. Increasing the exposure amount of the red light LR improves the image quality of the R image. The color enhancement process performed by the image generator 44 enables generating an image of high image quality.

The image sensor 34 is capable of separately reading out the R pixels, the G pixels, and the B pixels on a color-by-color basis as described above. The image sensor 34 performs the partial readout of the B pixel signals and the G pixel signals in accordance with emission end timing of the blue light LB and the green light LG at the time t1. Thereby increase of the noise in the B and G pixel signals due to the accumulation of unnecessary charges caused by dark currents and the like is prevented. The G pixels, in particular, are slightly sensitive also to the red light LR. Reading out the G pixel signals in accordance with the emission end timing of the green light LG effectively prevents the increase of the noise caused by the red light LR.

An operation of the above-configured endoscope system 10 is described. First, an operator inserts the insertion section 12a of the endoscope 12 in a body cavity. When or after the start of imaging is commanded by operating an operation panel or the like of the processor device 16, the first to third light sources 23a to 23c simultaneously starts the emissions of the blue light LB, the green light LG, and the red light LR, respectively. The emission intensities satisfy the relationship $I_B>I_G>I_R$. The red light LR, the green light LG, and the blue light LB are combined by the light integrator 24 into the white illumination light and supplied to the light guide 25. The white illumination light is emitted from the distal end portion 12d of the endoscope 12 to illuminate the object.

In accordance with the start of the emissions of the blue light LB, the green light LG, and the red light LR, all of the pixels rows of the image sensor 34 are sequentially reset on a pixel row by pixel row basis (sequential reset). After the lapse of the first exposure time $T_{E1}$ from the time t0, the image sensor performs the signal readout operation of the B pixels and the G pixels only (partial readout) to output digital B pixel signals and digital G pixel signals. The digital B and G pixel signals are inputted to the DSP 42 of the processor device 16. The second light source 23b and the third light source 23c stop the emissions of the green light LG and the blue light LB when the signal readout operation, which is performed by the image sensor 34, of the B and G pixels is finished.

After the lapse of the second exposure time $T_{E2}$ from the emission start time t0, the image sensor 34 performs the signal readout operation of the R pixels only (partial readout). Thereby the digital R pixel signals are outputted. The digital R pixel signals are inputted to the DSP 42 of the processor device 16. The first light source 23a stops the emission of the red light LR when the image sensor 34 finishes the signal readout operation of only the R pixels.

Then, the DSP 42 performs various types of image processing on the RGB image signals, which are composed of the B pixel signals, the G pixel signals, and the R pixel signals inputted from the image sensor 34. The noise remover 43 performs the noise removal process on the RGB image signals, which have been subjected to the signal processing performed by the DSP 42. Thereafter the RGB image signals are inputted to the image generator 44. Based on the RGB image signals inputted, the image generator 44 generates an image. The image is displayed on the monitor 18 through the video signal generator 45. The above-described operations are performed periodically and repeatedly until the operator commands the start of imaging. Thereby the images displayed on the monitor 18 are updated sequentially.

Figure 9:
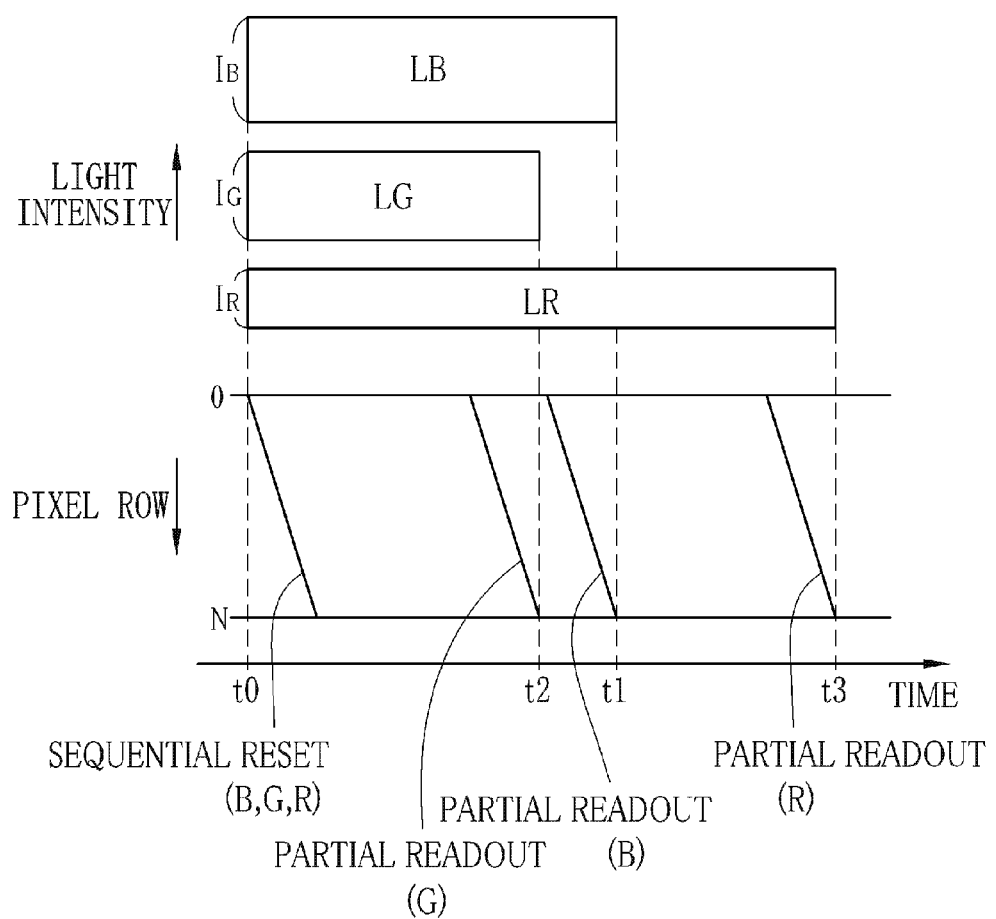
FIG. 9 illustrates emission timing and imaging timing in a case where emission end timing of blue light is different from that of green light.

In the above embodiment, as illustrated in FIG. 7, the emission end timing of the blue light LB is the same as the emission end timing of the green light LG. Note that the emission end timing of the blue light LB may differ from the emission end timing of the green light LG. For example, as illustrated in FIG. 9, in a case where "t1" denotes the time at which the emission of the blue light LB ends, "t2" denotes the time at which the emission of the green light LG ends, and "t3" denotes the time at which the emission of the red light LR ends, t1, t2, and t3 may satisfy the relationship t3>t1>t2. In this case, the image sensor 34 may perform the partial readouts to separately read out the B pixel signals, the G pixel signals, and the R pixel signals on a color-by-color basis in accordance with the emission end timing of each light.

Figure 10:
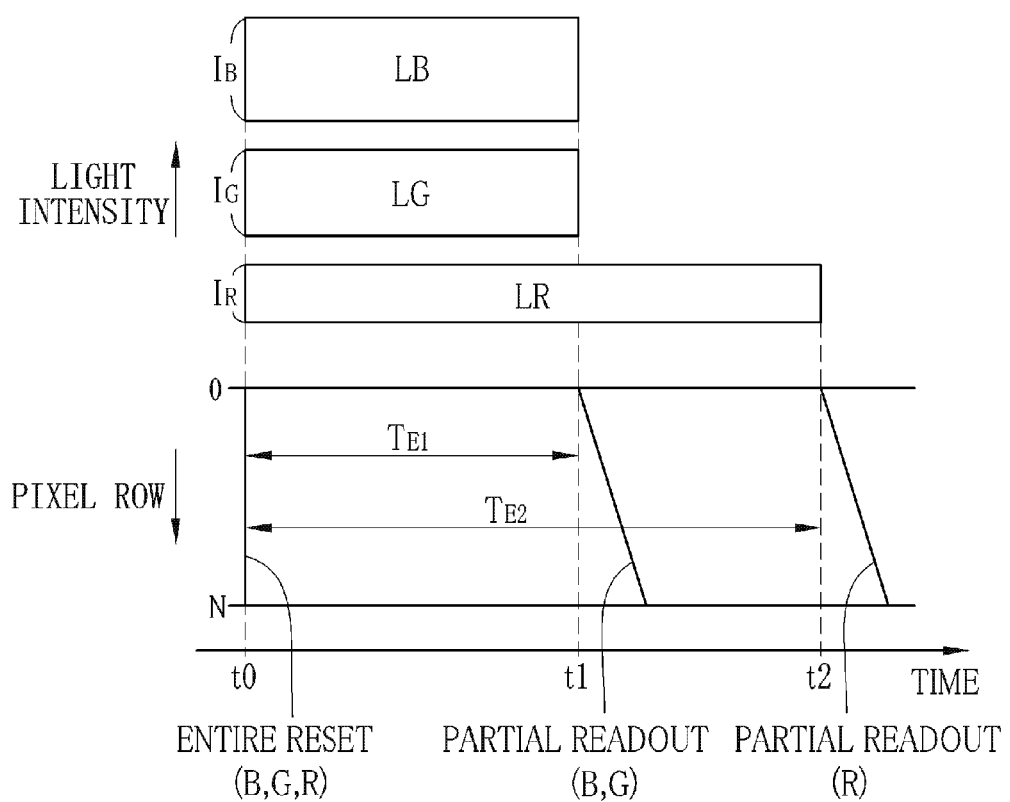
FIG. 10 illustrates emission timing and imaging timing of a global shutter.

In the above embodiment, the sequential reset is performed as illustrated in FIG. 7. Instead, the entire reset may be performed as illustrated in FIG. 10. In this case, the imaging controller 40 resets all of the pixel rows of the image sensor 34 through the entire reset at the time t0 at which the first to third light sources 23a to 23c start the emissions of the red light LR, the green light LG, and the blue light LB.

The light source controller 21 stops the emissions of the green light LG and the blue light LB at the time t1, at which the first exposure time $T_{E1}$ has elapsed from the time t0. From the time t1, the imaging controller 40 allows starting the signal readout operation of the B pixels and the G pixels only (partial readout). The imaging controller 40 stops the emission of the red light LR at the time t2, at which the second exposure time $T_{E2}$ has elapsed from the time t0. From the time t2, the imaging controller 40 allows starting the signal readout operation of the R pixels only (partial readout). Other than those, the operations are the same as or similar to those described in the above embodiment.

In FIG. 10, all of the pixel rows start receiving the light (storing the charges) after the entire reset as described above. In this case, exposure start timing of all the pixel rows is the same. Since the readout is performed after the end of the emission of the light of each color, exposure end timing of the pixel rows of the same color is the same. Hence, FIG. 10 shows a so-called global shutter, in which the light-receiving periods of the pixel rows of the same color are the same.

FIG. 7 illustrates a rolling shutter, so that the light-receiving period varies from pixel row to pixel row. FIG. 10 illustrates the global shutter, so that the light-receiving periods of the pixel rows of the same color are the same. In other words, the so-called synchronization is achieved. In addition to the synchronization, the global shutter illustrated in FIG. 10 enables longer first and second exposure times $T_{E1}$ and $T_{E2}$ and thereby increases the exposure amounts as compared with those of the rolling shutter.

Second Embodiment

In the first embodiment, the image sensor 34 is capable of separately performing the partial "readout" of the pixel signals of the pixels of each color. Thereby the image sensor 34 is capable of separately changing the light-receiving period (exposure time) of the light of each color. In the second embodiment, a partial "reset" is performed on a color-by-color basis to allow changing the light-receiving period of the light of each color separately.

Figure 11:
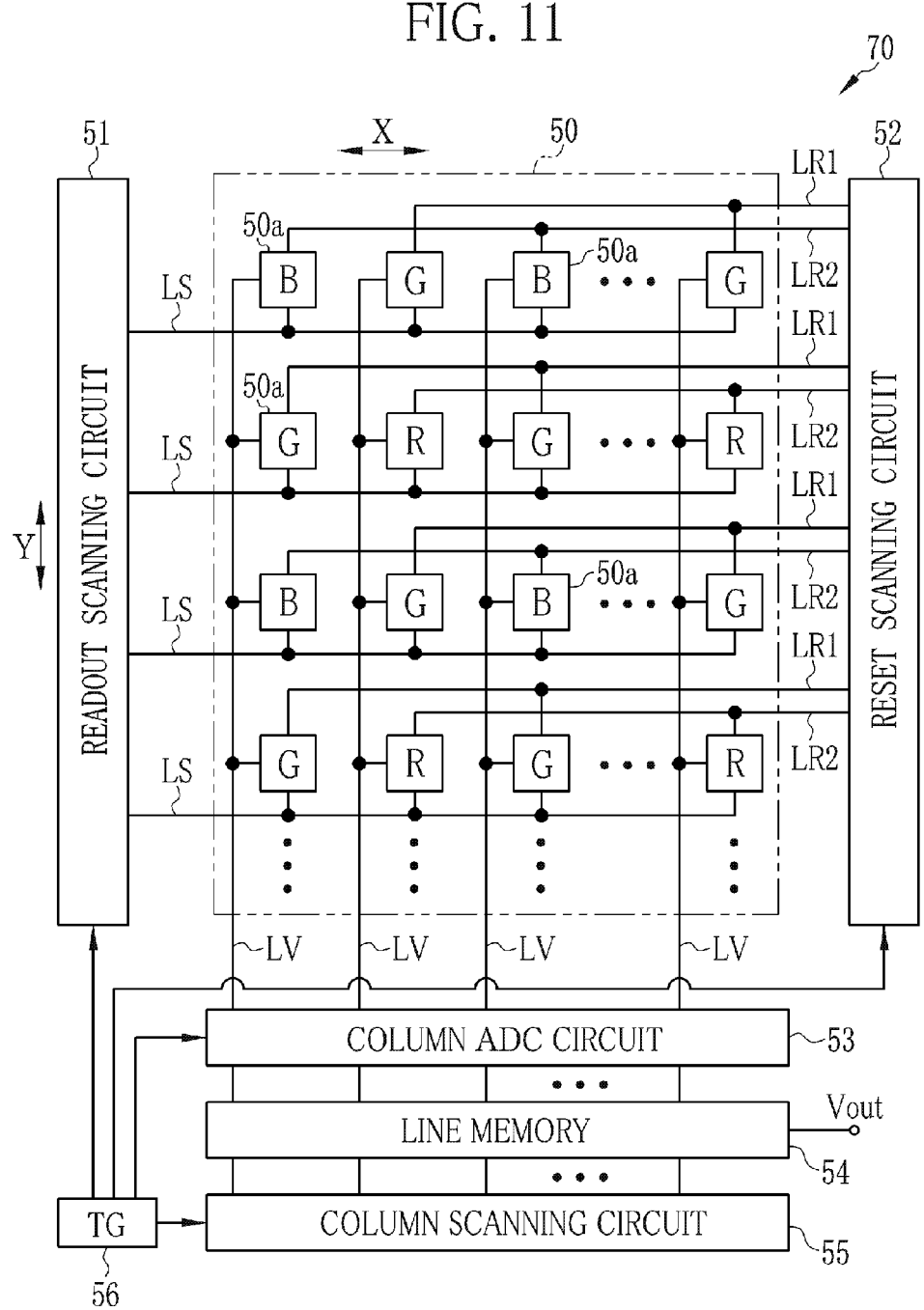
FIG. 11 illustrates configuration of the image sensor according to a second embodiment.
Figure 12:
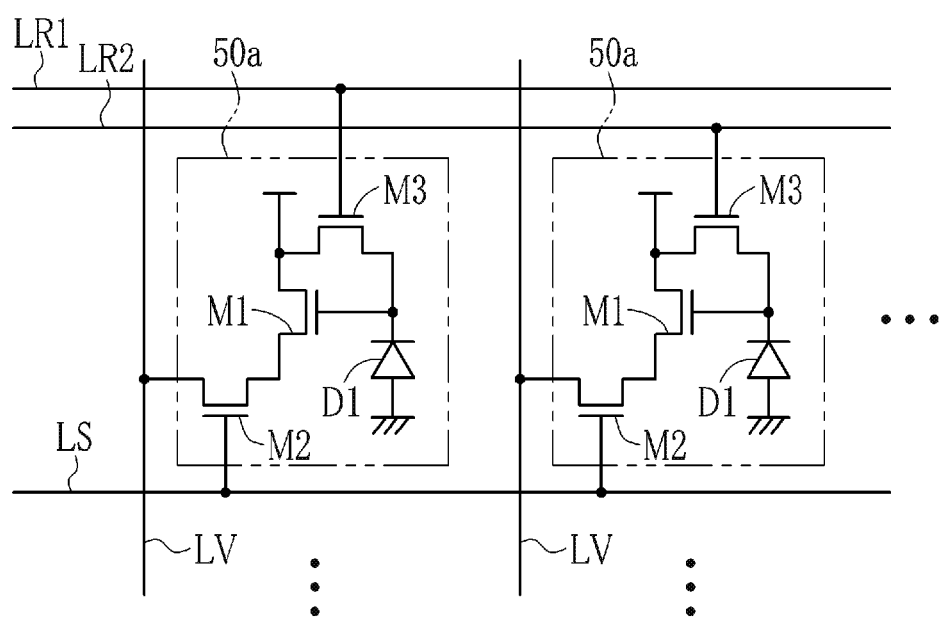
FIG. 12 illustrates configuration of pixels of the image sensor according to the second embodiment.

In the second embodiment, an image sensor 70 illustrated in FIGS. 11 and 12 are used in place of the image sensor 34 of the first embodiment. The image sensor 70 has a plurality of row selection lines LS. The pixels 50a in one pixel row are connected to a single corresponding row selection line LS. The image sensor 70 has first row reset lines LR1 and second row reset lines LR2. The G pixels of one pixel row are connected to a single corresponding first row reset line LR1. The B pixels of one pixel row are connected to a single corresponding second row reset line LR2. The R pixels of one pixel row are connected to a single corresponding second row reset line LR2.

During the signal readout operation, the readout scanning circuit 51 sequentially supplies the row selection signals to the respective row selection lines LS to allow "the sequential readout", by which the pixel signals are read out sequentially from each pixel row on a pixel row by pixel row basis. At the time of the reset operation, the reset scanning circuit 52 supplies the reset signal to the first row reset line LR1 or the second row reset line LR2. Thereby the pixels 50a connected to the first row reset line LR1 or the second row reset line LR2 to which the reset signal has been supplied are reset. Other than that, the configuration of the image sensor 70 is the same as or similar to that of the image sensor 34 of the first embodiment.

The image sensor 70 may simultaneously supply the reset signals to all of the first row reset lines LR1, respectively. Thereby only the G pixels are reset simultaneously. The image sensor 70 may simultaneously supply the reset signals to the second row reset lines LR2 of the even-numbered rows, respectively, thereby simultaneously resetting only the B pixels. The image sensor 70 may simultaneously supply the reset signals to the second row reset lines LR2 of the odd-numbered rows, respectively, thereby simultaneously resetting only the R pixels. The image sensor 70 may simultaneously supply the reset signals to all of the first and second row reset lines LR1 and LR2, thereby collectively and simultaneously resetting all the pixels of all the pixel rows.

Figure 13:
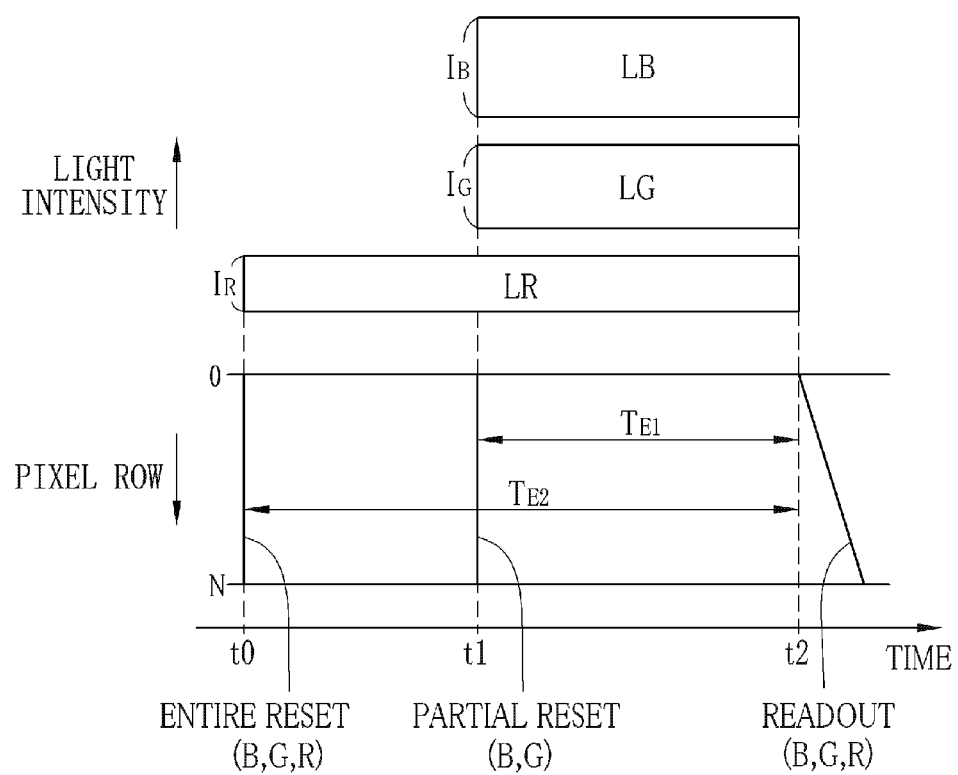
FIG. 13 illustrates the emission timing and the imaging timing in the second embodiment.

As illustrated in FIG. 13, in the second embodiment, the light source controller 21 allows the first light source 23a to start the emission of the red light LR from the time to. In accordance with the start of the emission of the red light LR at the time t0, the imaging controller 40 allows the image sensor 34 to collectively and simultaneously reset the pixels of all the pixel rows (entire reset). The light source controller 21 allows the second light source 23b and the third light source 23c to start the emissions of the green light LG and the blue light LB, respectively, from the time t1 while the emission of the red light LR is continued. In accordance with the start of the emissions of the green light LG and the blue light LB at the time t1, the imaging controller 40 allows the image sensor 34 to simultaneously reset the B pixels and the G pixels only (partial reset).

Thereafter, the light source controller 21 stops the emission operations of the first to third light sources 23a to 23c at the time t2, to end the emissions of the blue light LB, the green light LG, and the red light LR. From the time t2, the imaging controller 40 allows the image sensor 34 to start the sequential readout. Thereby all of the B pixels, the G pixels, and the R pixels are read out.

As described above, the second embodiment describes the global shutter. The period from the time t1 to the time t2 is the first exposure time $T_{E1}$ of the B pixels and the G pixels. The period from the time t0 to the time t2 is the second exposure time $T_{E2}$ of the R pixels.

In the second embodiment, the emissions of the blue light LB and the green light LG are started simultaneously from the time t1. Note that the emission timing of the blue light LB may differ from that of the green light LG. In this case, only the B pixels are reset in accordance with the emission start timing of the blue light LB and only the G pixels are reset in accordance with the emission start timing of the green light LG.

In the above embodiments, the emission periods of the red light LR, the green light LG, and the blue light LB partly overlap each other. In the emission periods overlapped, all of the red light LR, the green light LG, and the blue light LB are emitted. Alternatively, the emission periods of two of the red light LR, the green light LG, and the blue light LB may overlap each other and the remaining light may be emitted independently so as not to overlap the emission period of another light.

For example, the first embodiment may be modified as illustrated in FIG. 14. The green light LG is emitted, and then the emissions of the red light LR and the blue light LB are started after the emission of the green light LG is ended. Thereby the emission period of the green light LG does not overlap the emission periods of the red light LR and the blue light LB. In this case, the image sensor 34 simultaneously receives the red light LR and the blue light LB, whose wavelength ranges are apart from each other. Thereby the occurrence of color mixing is reduced.

The red light LR, the green light LG, and the blue light LB may be emitted separately and one after another with no overlapping emission periods.

The first embodiment uses the image sensor 34 capable of separately reading out the R pixels, the G pixels, and the B pixels on a color-by-color basis. The second embodiment uses the image sensor 70 capable of separately resetting the R pixels, the G pixels, and the B pixels on a color-by-color basis. Instead of the image sensors 34 and 70, an image sensor capable of separately reading out and separately resetting the R pixels, the G pixels, and the B pixels on a color-by-color basis may be used. In this case, the start timing and the end timing of the light-receiving period (exposure time) may be set freely for the pixels of each color, on a color-by-color basis.

In the above embodiments, the light source device 14 and the processor device 16 are provided separately. The light source device and the processor device may be provided integrally.

Various changes and modifications are possible in the present invention and may be understood to be within the present invention.

What is claimed is:

1. An endoscope system comprising:
a light source unit that emits each of first light, second light, and third light as illumination light, the first, second, and third light being different in color;
a light source controller configured to control emission intensity and emission timing of the illumination light to make an emission period of the first light longer than an emission period of each of the second light and the third light;
a simultaneous-type image sensor configured to separately and simultaneously receive light of the each color reflected from an object of interest irradiated with the illumination light and separately change a light-receiving period of the light of the each color; and
an imaging controller configured to make the light-receiving period of the first light on the simultaneous-type image sensor longer than the light-receiving period of each of the second light and the third light,
wherein the light source controller makes the emission intensity of the first light less than the emission intensity of each of the second light and the third light at a same time the emission period of the first light is longer than the emission period of each of the second light and the third light, and
wherein the first light is red light, the second light is green light, and the third light is blue light.

2. The endoscope system according to claim 1, wherein the light source controller makes emission start timing of the second light coincide with emission start timing of the third light.

3. The endoscope system according to claim 2, wherein the light source controller makes emission end timing of the second light different from emission end timing of the third light.

4. The endoscope system according to claim 3, wherein the light source controller ends the emission of the third light after ending the emission of the second light.

5. The endoscope system according to claim 1, wherein the imaging controller makes the light-receiving period of the first light on the simultaneous-type image sensor coincide with the emission period of the first light, and makes the light-receiving period of the second light on the simultaneous-type image sensor coincide with the emission period of the second light, and makes the light-receiving period of the third light on the simultaneous-type image sensor coincide with the emission period of the third light.

6. The endoscope system according to claim 1, wherein the simultaneous-type image sensor has pixels corresponding to the each color, and the imaging controller selectively reads out the pixels of one or two colors.

7. The endoscope system according to claim 1, wherein the light source controller controls emission periods of at least two of the first light, the second light, and the third light so as to at least partly overlap each other.

8. A method for operating an endoscope system, the endoscope system comprising a light source unit and a simultaneous-type image sensor, the light source unit being configured to emit each of first light, second light, and third light as illumination light, the first, second, and third light being different in color, the simultaneous-type image sensor being configured to separately and simultaneously receive light of the each color reflected from an object of interest irradiated with the illumination light and separately change a light-receiving period of the light of the each color, the method comprising the steps of:
controlling emission intensity and emission timing of the illumination light to make an emission period of the first light longer than an emission period of each of the second light and the third light; and
making the light-receiving period of the first light on the image sensor longer than the light-receiving period of each of the second light and the third light,
wherein the emission intensity of the first light is controlled to be less than the emission intensity of each of the second light and the third light at a same time the emission period of the first light is longer than the emission period of each of the second light and the third light, and
wherein the first light is red light, the second light is green light, and the third light is blue light.

* * * * *